(12) United States Patent
Soltyk

(10) Patent No.: US 6,635,865 B1
(45) Date of Patent: Oct. 21, 2003

(54) IMAGING SENSOR MICROASSEMBLY HAVING DUAL CIRCUIT BOARD FORMED OF UNSYMMETRICAL T SHAPE

(76) Inventor: Andrew J. Soltyk, 16 Blackwood Dr., Liverpool, NY (US) 13090

( * ) Notice: Subject to any disclaimer, the term of this patent is extended or adjusted under 35 U.S.C. 154(b) by 552 days.

(21) Appl. No.: 09/624,719

(22) Filed: Jul. 25, 2000

(51) Int. Cl.[7] .................................................. H01J 5/02
(52) U.S. Cl. ................................. 250/239; 250/208.1
(58) Field of Search ............................. 250/239, 208.1; 257/80–84, 291, 432–435, 676, 678, 684; 361/600, 748, 753, 760, 768, 772–774, 807

(56) References Cited

U.S. PATENT DOCUMENTS 5,748,448 A * 5/1998 Hokari ........................ 361/749
5,754,313 A   5/1998 Pelchy et al.

* cited by examiner

Primary Examiner—Que T. Le

(57) ABSTRACT

A Solid State Imaging Sensor Microassembly for miniature, remote head video cameras having small imaging sensor (10) and two circuits boards, top board (30) and bottom board (32). The imaging sensor of the type without a package and protected by the glass cover only, with leads (26) attached directly to the silicon chip (22). The sensor leads (26) bonded to opposite edges of the top board (30) placing the imager (10) in parallel alignment to the top board (30) some distance from it. Alternatively the packageless and leadless imaging sensor (12), bonded and connected to the top surface of the top circuit board (60) by the grid of small solder balls (66). Second circuit board (32) bonded perpendicularly and off center to the other side of top board (32) forming structure of an unsymmetrical capital T with one arm shorter than the other. In addition electronics components (34) are sandwiched between the imager (10) and top board (30) and still other components (38) are placed on one of the surfaces of the bottom board (32) which surface is facing away from the center of top board (30). Other surface of the bottom board (32) which is facing towards the center of the top board (30) has transmission cable conductors (36) attached.

9 Claims, 8 Drawing Sheets

ADDITIONAL EMBODIMENT

ADDITIONAL EMBODIMENT

ADDITIONAL EMBODIMENT

ALTERNATIVE EMBODIMENT

SECOND ALTERNATIVE

SECOND PRIOR ART

IMAGING SENSOR MICROASSEMBLY HAVING DUAL CIRCUIT BOARD FORMED OF UNSYMMETRICAL T SHAPE

CROSS-REFERENCE TO RELATED APPLICATIONS

Not applicable.

BACKGROUND

1. Field of Invention

This invention relates to solid state imaging sensor assemblies, specifically to a highly compact assemblies of remote head video cameras used in endoscopes, borescopes, laproscopes, diagnostic, inspection and monitoring devices.

2. Description of Prior Art

Medical diagnostic instruments such as endoscopes, gastroscopes, laproscopes, colonoscopes as well as industrial inspection tools like borescopes or monitoring devices, require video cameras of smallest possible dimensions. To achieve this goal remote head cameras are used in which small head with image sensor is separated from bigger video processing circuits. Long and of small diameter cable provides connection and communication between head and processor. Conventional methods of electronic components packaging presently yield imaging sensors measuring approximately 10 by 10 millimeters which defines head assembly cross-section and is far to big for the sophisticated medical and industrial applications. In an effort to reduce imaging sensor size, and allow for smaller remote head of the video camera, an advanced integrated circuits technologies are constantly being developed. One such technology (TAB—Tape Automated Bonding) provides leads of the packageless imaging sensor bonded directly to the silicon chip. The leads extend typically outward from two opposite edges of the imager for a distance sufficient to allow the leads to be connected to other components. A transparent window, typically being coated glass, is positioned over the imaging sensor, covering its surface together with the ends of the leads bonded to the silicon chip. Another technology (BGA—Ball Grid Array) produces similar imaging sensors but without leads altogether, with all necessary connections accomplished through small balls of solder formed on the bottom surface of packageless sensor. This class of processes allows reduction of the size of the sensor to approximately 3 by 3 millimeters or less. Imaging sensors of small size like ones described above are structurally week and require special assembly to lend themselves for use in the camera head. Two design configurations of such assembly are known so far, both described in U.S. Pat. No. 5,754,313 to Pelchy et al (1998). First prior art configuration is shown on FIG. 10. The image sensor 110 is centrally mounted upon the shorter edge of an elongated board 111. The imager leads 112, which extend outward from the imager are turned down and are bonded to either side of the board. A plastic resin is applied about the imager package and the board to bond the two together in an assembly. Other electronic components 113—113 are placed on either side of the board 111 to complete the assembly. Transmission cable conductors 115—115 connect this prior art imaging sensor assembly with the camera processing unit and are bonded to the board 111 at the end opposite to the imager 110. Although above described prior art imaging sensor assembly takes full advantage of the small cross-section of the imager, it nevertheless suffers from disadvantage of being unacceptably long. Because of the extended length, this prior art assembly does not lend itself well for the use in medical or industrial instruments, where tip of the instrument, housing the camera, must be articulated to maneuver the device around sharp corners or bends. Second prior art configuration is shown on FIG. 20. The image sensor 210 is mounted on a hybrid circuit board 211 above, and in the parallel alignment to it. Two additional hybrid boards 213 and 214 are placed perpendicularly beneath board 211 in opposite parallel alignment. Electronic circuitry 217—217 is mounted on the inside surfaces of the boards. Encapsulating plastic resin is placed between the boards to provide structural strength to the assembly. The leads 212 extending from the imager 210 are brought down and are bonded to outside faces of the boards 213 and 214. Transmission wires 215—215 being part of the cable which links imaging sensor assembly with processing part of the camera, are bonded to the same outer faces of the hybrid boards just under imager leads 212. This second configuration of the prior art imaging sensor (FIG. 20) assembly attempts to overcome the problem of length in the first configuration (FIG. 10), but brings several new deficiencies.

(a) First weakness is that second prior art imaging sensor assembly has to be build with the expensive hybrid technology not leaving any opportunity to the use of potentially less costly conventional, packaged components, materials or assembly methods. Assembly is composed of three separate hybrids 211, 213 and 214 put together to form one part.

(b) Second, more serious disadvantage, is the placement of a transmission cable conductors 215 on both outer surfaces of the assembly at the end opposed to the imager 210. Starting from the two different places separated by the full width of the assembly, cables are coming together into one bundle some distance from the back of the assembly. This arrangement forms a rigid triangle 220, formed by the back of the assembly and two sets of cable conductors approching from two sides of the assembly. This design is effectively extending bending capabilities of the cable farther away from the assembly. In practice it works like extending length of the assembly some distance behind the physical length of it, effectively nullifying potential advantages of the shorter assembly.

SUMMARY

In accordance with the present invention an imaging sensor microassembly compromises of packageless solid state imaging sensor and two boards mounted perpendicularly to each other. Image sensor is mounted in parallel alignment on or above top surface of the top board. Sensor of the type with the leads has them bonded to the opposite edges of that top board. Leadless sensor mounts directly to the surface of the top board. Bottom board is being attached to the other side of the top board, with electronics components placed, space permitting, on the surface of the top board under the imaging sensor. The other components are placed on the one of the surfaces of the bottom board, with the transmission cable conductors attached to the other surface of the bottom board. Bottom board is mounted perpendicularly to the top board not in the center of its surface, but slightly off to one side. This arrangement lives more space to the electrical transmission conductors and allows for the central, symmetrical placement of conductors, lending to best possible bending properties of the assembly.

Objects and Advantages

Accordingly the objects and advantages of the present invention are:

(a) to provide an imaging sensor microassembly which can satisfy size requirements (cross-section and length) of medical and industrial inspection devices like endoscopes or borescopes.

(b) to provide an imaging sensor microassembly which can incorporate microminiature packageless imaging sensor with leads bonded directly to the silicon chip or leadless and, at the same time, will not require, but also not exclude, expensive aterials and components or complicated assembly methods like hybrid technology.

(c) to provide an imaging sensor microassembly with the transmission cables positioned close to the center of the assembly cross-section to allow for the cable to bent in the close proximity to the assembly.

Further object of the present invention is to provide a compact imaging sensor microassembly for video endoscopes, borescopes, laproscopes, diagnostic and monitoring devices that is rugged, insensitive to ambient conditions, simple to use and inexpensive. Still further objects and advantages will become apparent from a consideration of the ensuing description and drawings. These and other objects of the present invention are attained by means of an imaging sensor microassembly suitable for use in the small diameter diagnostic, monitoring and inspection instruments. The assembly includes miniature packageless imager, with the leads bonded directly to the silicon chip or leadless. The assembly includes also two circuit boards. Boards are mounted perpendicularly to each other with the image sensor mounted in parallel alignment to the top surface of the top board. The leads of the sensor are bonded to the two opposite edges of the top board. Leadless sensor mounts directly to the top board. Second, bottom board is attached to the other side of the first board in the pattern resembling capital T, but moved slightly off center to one side. Electronic components are mounted on the surface of the first board under the imager and—or on one side of the second board. The cable conductors are attached to the opposite surface of the second bottom board which is facing towards the center of the assembly. This arrangement puts the cable conductors in the center of the assembly aiding in bending properties of the cables.

DRAWING FIGURES

For a better understanding of these and other objects of the present invention the following description of the invention is to be read in association with the following drawings, wherein.

Figure 1:
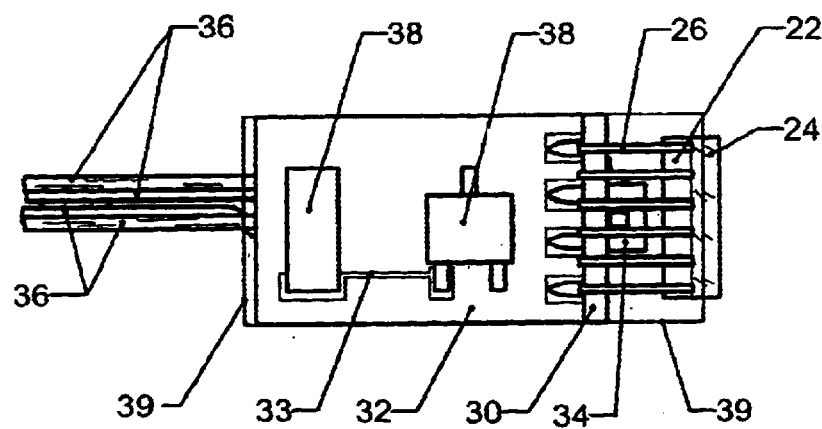
FIG. 1 is a side view of the imager microassembly shown embodying the teachings of the present invention

Reference Numerals In Drawings 10 imaging sensor (imager)
12 leadless imaging sensor (imager)
22 silicone chip
24 glass cover
26 imager leads
30 top board
32 bottom board
33 conductive metallic traces
34 top board electronic components
36 cable conductors
37 metallic pattern
38 bottom board electronic components
39 plastic resin encapsulation
44 electronic components in a die (chip) form on the top board (additional embodiment).
48 electronic components in a die form on the bottom board.
50 top circuit board in an alternative embodiment
52 bottom board in an alternative embodiment
60 top board for leadless imager
66 solder balls of Ball Grid Array

DESCRIPTION—FIGS. 1,2,3 and 4—Preferred Embodiment

Figure 2:
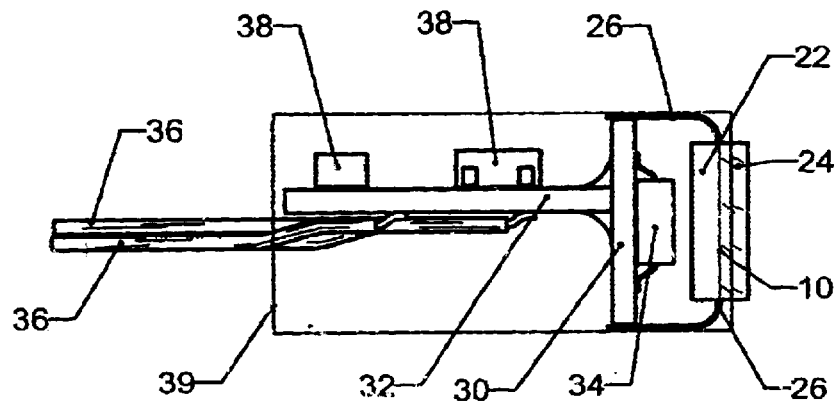
FIG. 2 is an end view showing the imager microassembly shown in FIG. 1.
Figure 3:
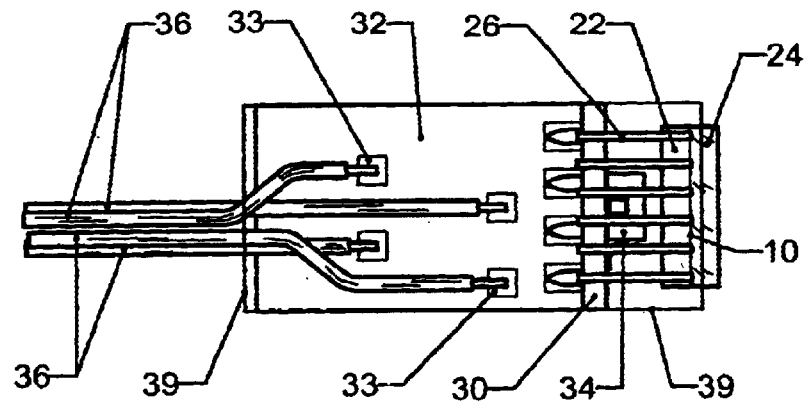
FIG. 3 is the other side view of the imager microassembly shown in FIG. 1

Preferred embodiment of the imaging sensor microassembly is illustrated in FIG. 1, FIG. 2 and FIG. 3. The imaging sensor microassembly includes an imager 10 that has a CCD silicon chip 22 covered with a protecting glass window 24. A number of thin leads 26—26 extend from two opposite edges of the imager. The leads 26—26 are bend downward and bonded to the opposites edges of top board 30. The size of the board 30 is about equal or slightly bigger than the size of the imager. Board 30 is positioned in parallel alignment under the imager 10 at the distance of 2 mm or less. This distance creates the space needed to place the electronic components 34—34 on board 30 under the imaging sensor. Further away from the imager 10, a second, bottom board 32 is attached perpendicularly to the top board 30. Placement is slightly off centre of the surface of the top board 30 opposite to the imaging sensor. Bottom board 32 is positioned closer to one edge of board 30 and farther away from the other edge. Cable conductors 36—36 are bonded to one surface of the bottom board 32 which is facing towards the center of board 30. Other surface of bottom board 32 which is facing away from the center of board 30 is used to accommodate electronics components 38—38. This embodiment of the invention creates an asymmetrical structure of an imaging assembly which allows for placement of the transmission cable conductors 36—36 in or close to the center of the microassembly. Width of the board 32 is the same as board 30. Length of the board 32 is 15 mm or less, as needed to provide enough space for electronics components 34—34. The boards are constructed from a nonconductive material, being paper epoxy, glass epoxy or ceramics with conductive metallic traces 33—33 on the surface or within, providing all necessary connections between boards 30 and 32, imaging sensor and components 34—34 and 38—38. As illustrated on FIG. 4 metallic pattern 37 on both sides of one shorter edge of bottom board 32 and on the surface of the top board 30 facing away from the imager 10 and slightly off the center of that surface, allows for bonding boards 30 and 32 together in the shape of unsymmetrical capital T with one arm shorter than the other. Electronic circuit components 34—34 are mounted on the top surface of the board 30 under the imager, and 38—38 on one side of the bottom board 32. Electronic components 34—34 and 38—38 are of industry standard surface mount types in small packages. The surface of the bottom board 32, opposite to the one with electronics components 38—38, serves as bonding area for the cable conductors 36—36 which connect imager sensor microassembly with the processing unit. To protect the imaging sensor microassembly both mechanically and from the elements and to provide for heat evacuation it is encapsulated in the plastic resin 39.

Figure 5:
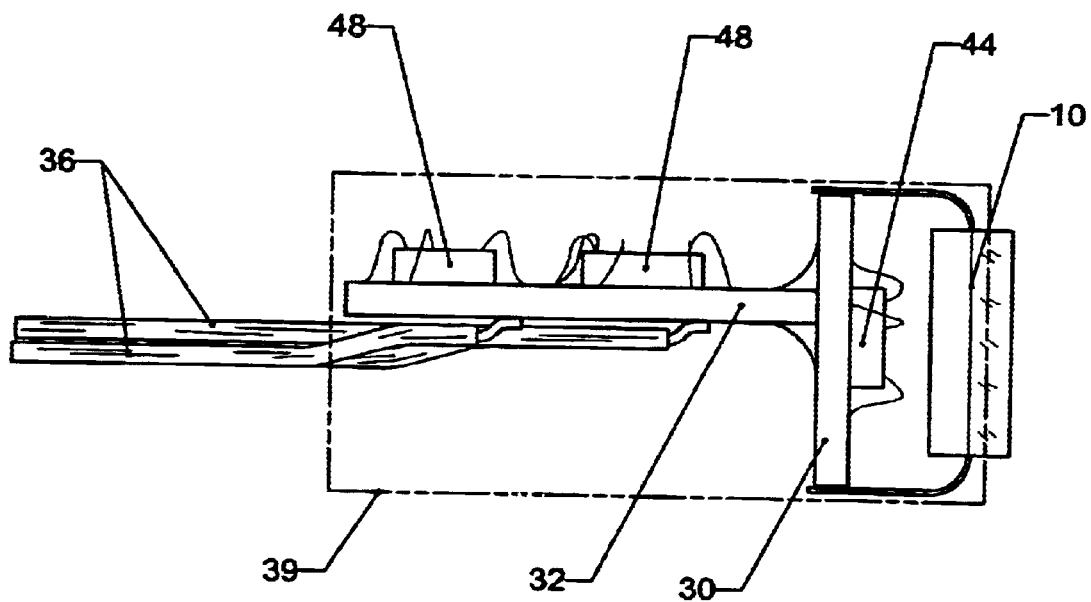
FIG. 5 is an additional embodiment of an imaging sensor microassembly.
Figure 6:
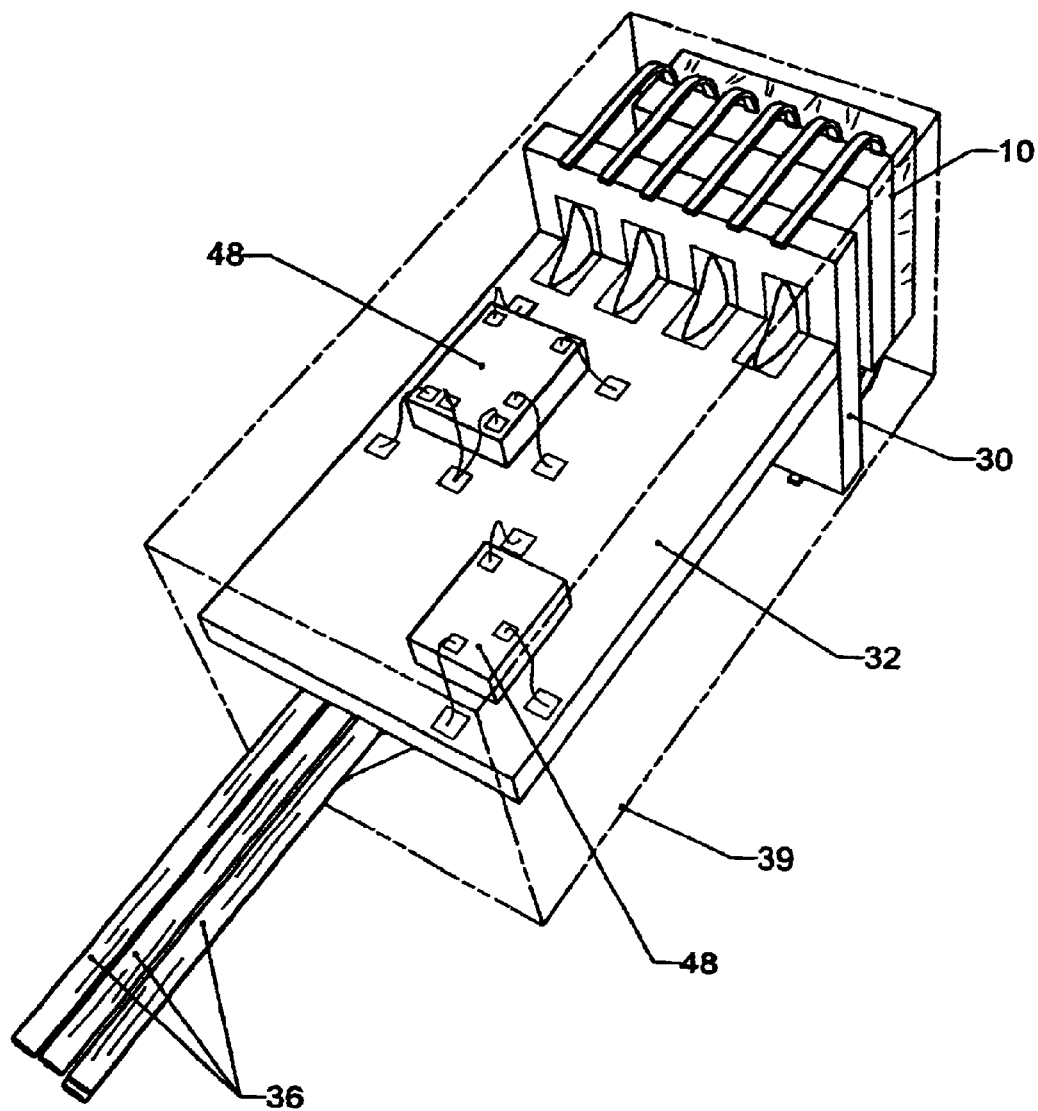
FIG. 6 is a perspective view of the additional embodiment of the imager microassembly.

FIG. 5 and FIG. 6—Additional Embodiment

Figure 4:
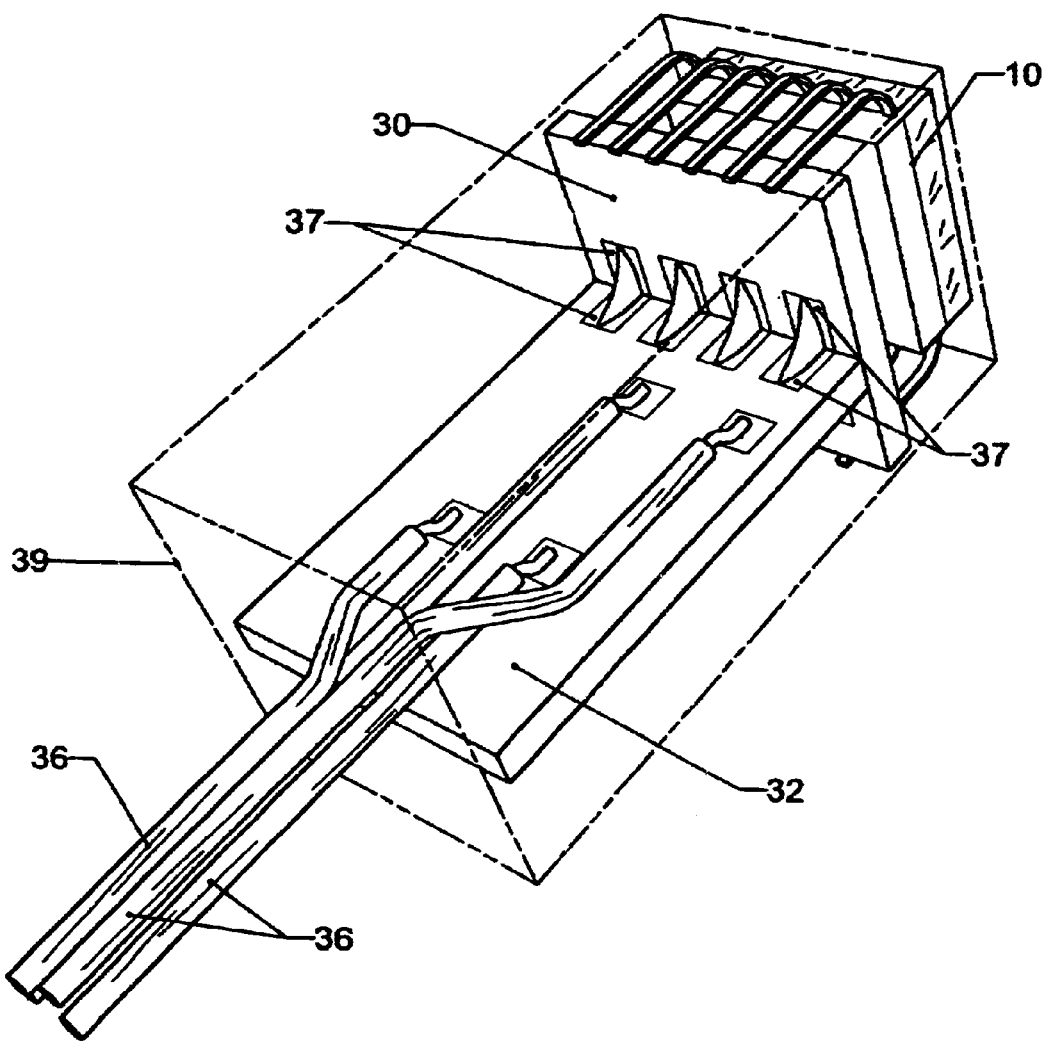
FIG. 4 is a perspective view of the microassembly showing the two boards bonded together.

Additional embodiment is shown in FIG. 4 and FIG. 5. In this case in place of the packaged surface mount electronics components (FIG. 2 34—34, 38—38), bare components 44—44, 48—48 without packages, called chips or dies are used. Technique known as wire bonding is used to connect electronic components 44—44, 48—48 to conducting metal traces on the boards 40 and 42. Electronic components 44—44 are placed on the surface of the top board 30 under the imaging sensor 10. Still other components 48—48 are positioned on one side of the bottom board 32 while the other surface is used to bond transmission cables 36—36.

Figure 7:
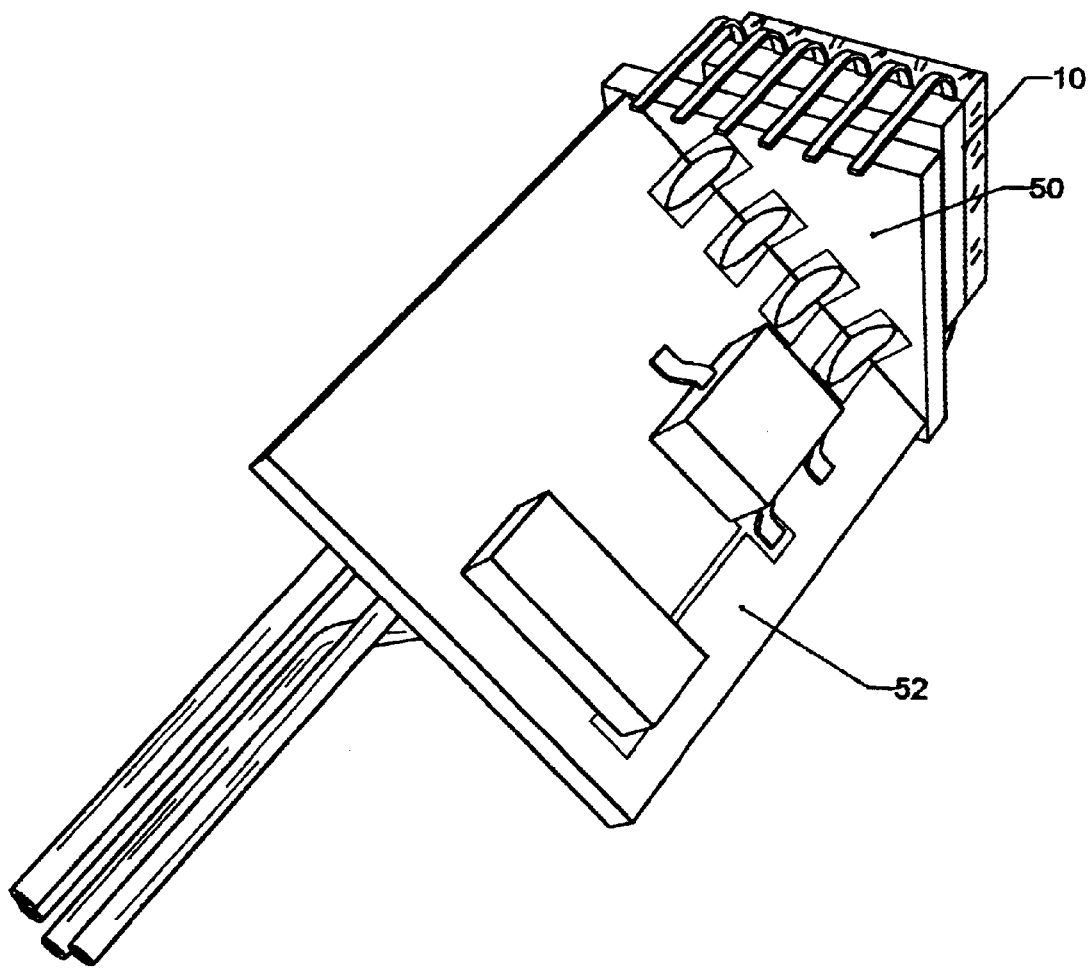
FIG. 7 shows a perspective view of the alternative embodiment of the imaging sensor microassembly.

FIG. 7—Alternative Embodiment

There are various possibilities with regard to the positioning of the second, bigger, bottom board 52 in respect to smaller, top board 50. If more space is needed for the electronic components, bottom board 52 can be placed perpendicularly to the top board 50 and, at the same time, along the diagonal of top board 50. This arrangement will allow for the maximum possible bottom board 52 area without scarifying overall size of the imager assembly.

Figure 8:
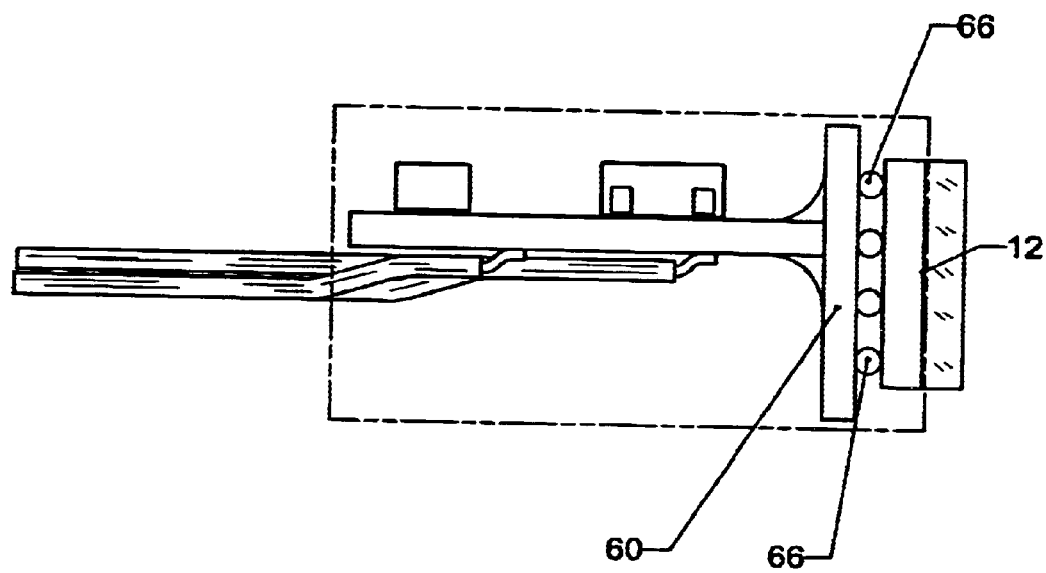
FIG. 8 shows a second alternative embodiment of the imaging sensor microassembly with the leadless imaging sensor.
Figure 9:
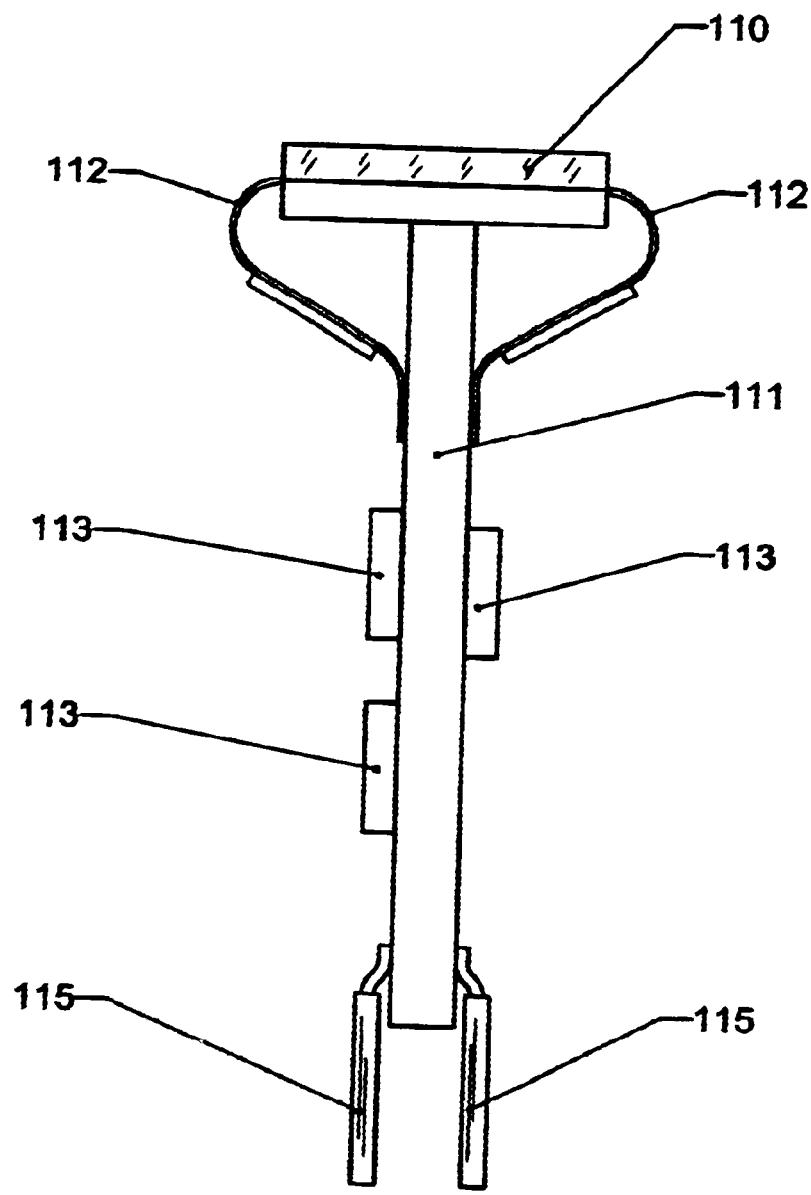
FIG. 9 shows a prior art imaging sensor assembly.
Figure 10:
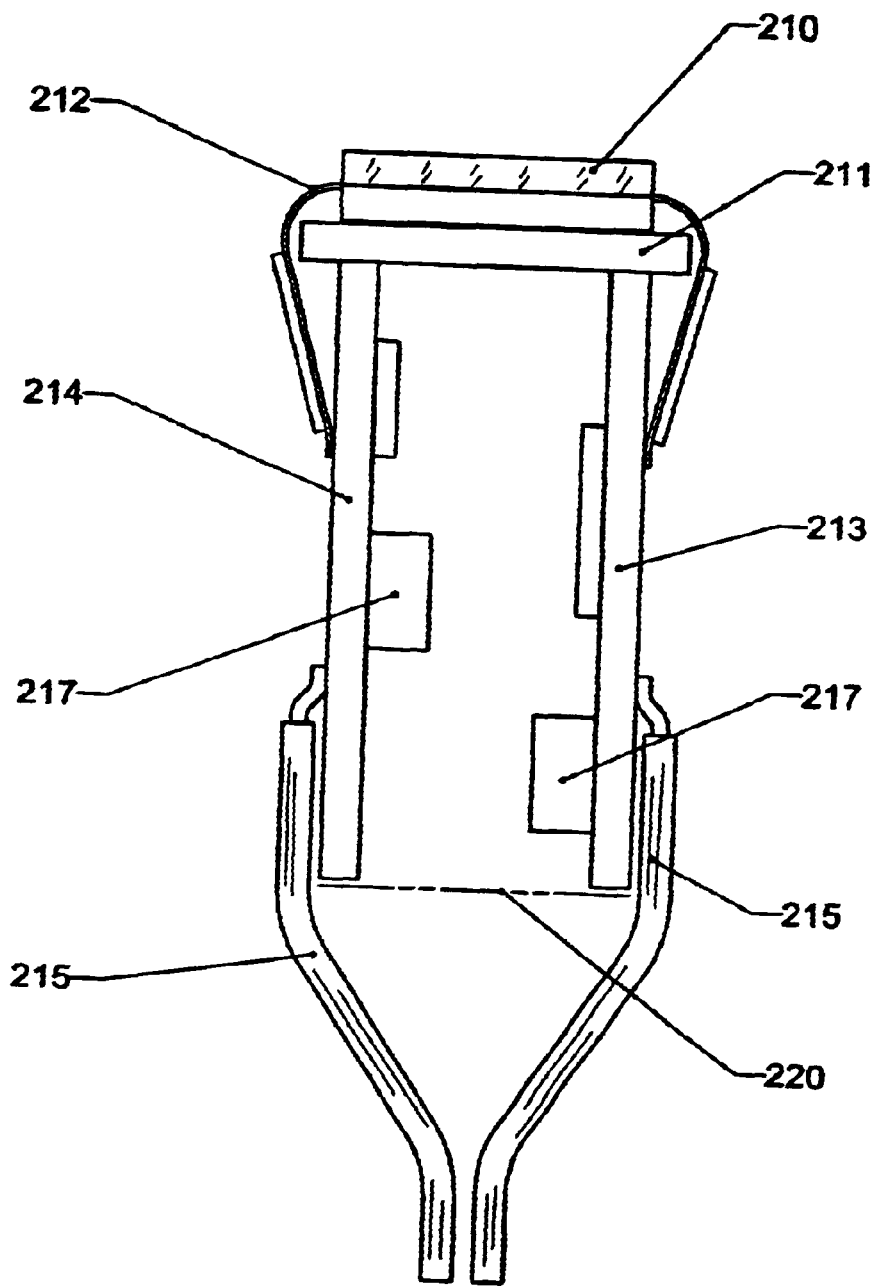
FIG. 10 shows another prior art imaging sensor assembly.

FIG. 8—Second Alternative Embodiment

Instead of the packageless imaging sensor with the leads it is possible to use leadless type of the sensor 12. This type of packaging uses grid of small solder balls 66 on the bottom surface of the sensor as connecting means. This embodyment requires placement of the imaging sensor 12 directly on the top surface of the top board 60. Bonding process connects solder balls 66 with the metallic pattern on the board 62.

Advantages

From the description above, a number of advantages of present solid state imager microassembly become evident:

(a) A very small solid state imaging microassembly which can satisfy size requirements (cross-section and length) of diagnostic, monitoring and inspection devices can be constructed.

(b) An imaging sensor microassembly can be provided which incorporates miniature imaging sensors with leads bonded directly to the silicon chip, or leadless one, and not require, but also not exclude, expansive materials, components and processes, hybrid technology being an example.

(c) An imager microassembly allowing, thanks to the asymmetrical structure of participating circuit boards, for placement of the transmission conductors close to the center of the assembly, permitting for the cable to bend in the close proximity to the assembly.

(d) An imaging sensor microassembly which maximizes circuit board area available for the electronic components by placing bigger board of the assembly along diagonal of the smaller one.

Conclusion, Ramification, and Scope

Accordingly, it can be seen that the imaging sensor microassembly of this invention can be easy and conveniently used in multitude of diagnostic, monitoring and inspection video instruments, both medical and industrial, where smallest possible size is of prime importance. Furthermore the imager assembly of present invention has the advantages in that:

it permits to produce very small video camera head using not only, typical in such a case, hybrid technology but lower cost epoxy board technique with standard surface mount packaged electronics components, as well.

it allows to place transmission cables, which provide all necessary signals for the assembly, in the proximity to the center of the assembly, aiding in cable bending, which is important for this type of devices.

Although the description above contains many specificities, these should not be construed as limiting the scope of the invention but as merely providing illustrations of some of the presently preferred embodiments of this invention. For example the imaging microassembly can have other shapes, such as round, triangular etc. Thus the scope of the invention should be determined by the appended claims and their legal equivalents, rather than the examples given.

What is claimed is:

1. A solid state imaging sensor microassembly that includes a solid state imaging sensor device with leads bonded directly to a silicon chip under a protective glass covering, a first, top circuit board placed under and in parallel alignment to said imaging sensor with one surface facing towards said sensor and having leads of said sensor bend down and bonded to the opposite edges of said top circuit board, a second, bottom circuit board bonded perpendicularly to the other surface of said top board, unsymmetricaly, slightly off centre of said surface of said top board, forming the structure of unsymmetrical T.

2. The solid state imaging sensor microassembly of claim 1 that further includes packaged electronic components sandwiched between said imaging sensor and said top board and bonded to conducting metallic traces on said top board.

3. The solid state imaging sensor microassembly of claim 1 that further includes packaged electronics components on one side of said bottom board bonded to conducting metallic traces on said bottom board.

4. The solid state imaging sensor microassembly of claim 1 that further includes electrical transmission conductors bonded to conducting metallic traces on the other side of said bottom board.

5. The solid state imaging sensor microassembly of claim 1 where said electrical transmission conductors are attached to the surface of said bottom board facing towards the center of said top board and said electronics components on the other side of said bottom board are facing away from the center of said top board.

6. The solid state imaging sensor microassembly of claim 1 where said top and bottom boards are encapsulated in plastic resin.

7. The solid state imaging sensor microassembly of claim 1 where said electronic components are without packages in die or chip form.

8. The solid state imaging sensor microassembly of claim 1 where said bottom board is bonded perpendicularly to said top board along the diagonal of said top board.

9. The solid state imaging sensor microassembly of claim 1 where said imaging sensor of packageless design has no leads and is mounted on the top surface of said top board by means of a grid array of solder balls.

* * * * *